United States Patent
Schmaus et al.

(10) Patent No.: US 9,655,824 B2
(45) Date of Patent: May 23, 2017

(54) USE OF DIPHENYLMETHANE DERIVATIVES AS TYROSINASE INHIBITORS

(75) Inventors: Gerhard Schmaus, Höxter-Bosseborn (DE); Martina Herrmann, Holzminden (DE); Holger Joppe, Dassel (DE); Gabriele Vielhaber, Holzminden (DE)

(73) Assignee: Symrise AG, Holzminden (DE)

(*) Notice: Subject to any disclaimer, the term of this patent is extended or adjusted under 35 U.S.C. 154(b) by 2984 days.

(21) Appl. No.: 10/558,364

(22) PCT Filed: May 24, 2004

(86) PCT No.: PCT/EP2004/050896
§ 371 (c)(1),
(2), (4) Date: Nov. 14, 2006

(87) PCT Pub. No.: WO2004/105736
PCT Pub. Date: Dec. 9, 2004

(65) Prior Publication Data
US 2007/0098655 A1   May 3, 2007

(30) Foreign Application Priority Data
May 30, 2003 (DE) .................. 103 24 566

(51) Int. Cl.
| | | |
|---|---|---|
| *A61K 8/00* | (2006.01) |
| *A61Q 17/04* | (2006.01) |
| *A61Q 19/00* | (2006.01) |
| *A61K 8/34* | (2006.01) |
| *A61Q 5/08* | (2006.01) |
| *A61Q 19/02* | (2006.01) |
| *A23L 5/41* | (2016.01) |

(52) U.S. Cl.
CPC .............. *A61K 8/347* (2013.01); *A23L 5/41* (2016.08); *A61Q 5/08* (2013.01); *A61Q 19/02* (2013.01); *A61K 2800/782* (2013.01)

(58) Field of Classification Search
USPC .......................................... 424/59
See application file for complete search history.

(56) References Cited

U.S. PATENT DOCUMENTS

| | | |
|---|---|---|
| 5,202,141 A | 4/1993 | McEvily |
| 5,399,785 A | 3/1995 | Miura |

FOREIGN PATENT DOCUMENTS

| | | |
|---|---|---|
| EP | 0 423 470 A1 | 8/1990 |
| EP | 0 811 595 A1 | 12/1997 |
| JP | 05-222200 | 8/1993 |
| JP | 06-056641 | 3/1994 |
| JP | 06-100433 | 4/1994 |
| JP | 06-508034 | 9/1994 |
| JP | 07-206699 | 8/1995 |
| JP | 11-506155 | 6/1999 |
| JP | 11-255637 | 9/1999 |
| WO | WO 00/56279 | 9/2000 |
| WO | WO 03/049713 A1 | 6/2003 |

OTHER PUBLICATIONS

Yamamura, T., Antioxidant Activities of Dihydric Phenol Derivatives for the Autoxidation of Tetralin, Bulletin of the Chemical Society of Japan, vol. 68, Issue 10, pp. 2955-2960.*
JP11-255,637, English Translation of Foreign Patent JP 11-255,637, listed on IDS dated Aug. 17, 2009, 10 pages.*

* cited by examiner

*Primary Examiner* — Alton Pryor
(74) *Attorney, Agent, or Firm* — Dilworth & Barrese, LLP

(57) ABSTRACT

Novel uses of compounds of the Formula 1 or mixtures of substances that contain one more compounds of the Formula 1,

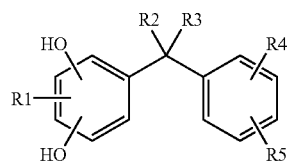

are described. The said compounds are suitable as agents against skin and hair browning, for combating age spots and for the inhibition of the undesired browning of foods.

9 Claims, No Drawings

USE OF DIPHENYLMETHANE DERIVATIVES AS TYROSINASE INHIBITORS

The present invention relates to the use of diphenylmethane derivatives of the following Formula 1 as tyrosinase inhibitors,

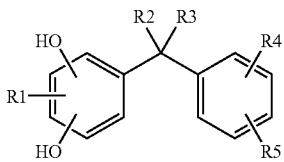

where:
R1 is
  hydrogen,
  methyl,
  straight-chain or branched, saturated or unsaturated alkyl having 2-4 C atoms
  OH or
  halogen,
R2 is
  hydrogen,
  methyl or
  straight-chain or branched, saturated or unsaturated alkyl having 2-5 C atoms,
R3 is
  methyl or
  straight-chain or branched, saturated or unsaturated alkyl having 2-5 C atoms,
and
R4 and R5 independently of one another are
  hydrogen,
  methyl,
  straight-chain or branched, saturated or unsaturated alkyl having 2-5 C atoms
  OH or
  halogen.

In this formula the substituents OH, R1, R4 and R5 can in each case, (as is shown in the drawing) assume an arbitrary position on the aromatic ring concerned (ortho, meta or para with respect to the bridge between the rings).

BACKGROUND OF THE TECHNOLOGY

In the field of the cosmetics industry there is an increasing need for agents for lightening skin and hair and for agents for combating age spots. In this context, cosmetics for lightening skin and hair and for combating age spots play a major role in particular in Asiatic countries with a dark skinned/haired population, but agents for such cosmetic treatments are gaining in importance in the central European area and in the USA as well.

The skin and hair colour of people is essentially determined via the melanocyte count, by the melanin concentration and the intensity of the melanin biosynthesis, in which context, on the one hand, intrinsic factors such as the genetic make-up of an individual and, on the other hand, extrinsic factors such as, in particular, the intensity and frequency of exposure to UV exert a significant influence on the skin and hair colour.

Skin-lightening active compounds usually intervene in the melanin metabolism or catabolism. The melanin pigments, which as a rule are brown to black in colour, are formed in the melanocytes of the skin, transferred into the keratinocytes and give rise to the colouration of the skin or the hair. In mammals, the brown-black eumelanins are formed mainly from hydroxy-substituted aromatic amino acids such as L-tyrosine and L-DOPA and the yellow to red pheomelanins are additionally formed from sulphur-containing molecules (Cosmetics & Toiletries 1996, 111 (5), 43-51). Starting from L-tyrosine, L-3,4-dihydroxyphenylalanine (L-DOPA) is formed by the copper-containing key enzyme tyrosinase, which L-3,4-dihydroxyphenylalanine, in turn, is converted by tyrosinase to dopachrome. The latter is oxidised to melanin via several steps catalysed by various enzymes.

Skin-lightening agents are used for various reasons: if the melanin-forming melanocytes in the human skin are not uniformly distributed for whatever reason, pigment spots are produced that are either lighter or darker than the surrounding areas of the skin. In order to eliminate this problem, lightening agents are used that help at least partially to even out such pigment spots. In addition, for many people there is a need to lighten their naturally dark skin colour or to prevent skin pigmentation. Very reliable and effective skin and hair lightening agents are needed for this purpose. Many skin and hair lightening agents contain tyrosinase inhibitors that are more or less powerful. However, this is only one possible route for skin and hair lightening.

Occasionally, UV-absorbing substances are also used for protection against the increase in skin pigmentation induced by UV light. However, this is an effect of purely physical origin and thus differs from the biological action of skin lightening agents on the cellular melanin formation, which is detectable even in the absence of UV light. Specifically, only the UV-induced browning of the skin can be prevented by UV filters, in contrast to which a lightening of the skin can also be produced by biologically active skin lighteners, which intervene in the melanin biosynthesis.

Hydroquinone, hydroquinone derivatives, such as, for example, arbutin, vitamin C, derivatives of ascorbic acid, such as, for example, ascorbyl palmitate, kojic acid and derivatives of kojic acid, such as, for example, kojic acid dipalmitate, are used in particular in commercially available skin and hair lightening agents.

One of the skin and hair lightening agents most frequently used is hydroquinone. However, the substance has a cytotoxic effect on melanocytes and acts as an irritant on the skin. Therefore, for example in Europe, Japan and South Africa, such preparations are no longer permissible for cosmetic applications. Moreover, hydroquinone is highly sensitive to oxidation and can be stabilised in cosmetic formulations only with difficulty.

Vitamin C and ascorbic acid derivatives have only an inadequate action on the skin. Moreover, they do not act directly as tyrosinase inhibitors, but reduce the coloured intermediates in the melanin biosynthesis.

Kojic acid (5-hydroxy-2-hydroxymethyl-4-pyranone) is a tyrosinase inhibitor that inhibits the catalytic action thereof via chelation of the copper atoms of the enzyme; it is used in commercial skin and hair lightening agents, but has a high sensitising potential and causes contact allergies.

In the search for novel agents that have a skin and hair lightening action and/or are active against age spots, the aim is, accordingly, quite generally to find substances that inhibit the enzyme tyrosinase in as low a concentration as possible, it furthermore having to be taken into account that these substances used in cosmetic and/or pharmaceutical products, in addition to having a high activity at concentrations that are as low as possible, must also be toxicologically acceptable,
readily tolerated by the skin and in particular not sensitising and not irritant,
stable (in particular in the customary cosmetic and/or pharmaceutical formulations),
preferably odourless and
able to be produced inexpensively (that is to say using standard methods and/or starting from standard precursors).

The search for suitable (active) substances that have one or more of the said properties to an adequate degree is made more difficult for the person skilled in the art because there is no clear dependence between the chemical structure of a substance, on the one hand, and its biological activity and its stability, on the other hand. Furthermore, there is no predictable relationship between the skin lightening effect, the toxicological acceptability, the tolerance by the skin and/or the stability of potential active compounds. Furthermore, a particular prerequisite for the use of an active substance in practice is its stability to chemical substances which are customarily used as accompanying constituents in cosmetics and to light.

SUMMARY OF THE INVENTION

The primary aim of the present invention was, therefore (in accordance with the general requirements, see above), to indicate an active substance which (a) has a good skin lightening effect (that is to say, for example, a powerful tyrosinase-inhibiting action in specific cell-free or cellular in vitro test systems, cellular in vitro test systems being preferred because of the better transference to the human in vivo situation), (b) can be prepared in a highly pure form, (c) is dermatologically and toxicologically acceptable and (d) in addition shows good stability to the effects of light. The Applicant's own research now showed that diphenylmethane derivatives of the Formula 1 achieve these aims and thus can be used preferentially as tyrosinase-inhibiting agents.

In this context, diphenylmethane derivatives that can be used according to the invention, such as, for example, styrylresorcinol (Formula 4; CARN:85-27-8; 4-(1-phenylethyl)-1,3-dihydroxybenzene), that is described in more detail below, can be prepared without any problem in accordance with methods known from the literature. To perform activity studies, the diphenylmethane derivatives of the Formula 1 were prepared by Friedel-Crafts alkylation in accordance with methods known from the literature, such as in T. Yamamura et al. (Bull. Chem. Soc. Jpn. Vol. 68, S.2955-2960; 1995).

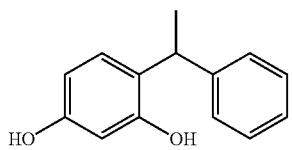

4

The Applicant's own research now showed that diphenylmethane derivatives of the Formula 1, and here in particular styrylresorcinol of the Formula 4, have a more powerful tyrosinase-inhibiting activity than hexylresorcinol that is used, inter alia, in the food industry as a browning inhibitor (see below, Example 1, Table 2: Comparison of styrylresorcinol (Formula 4) and 4-hexylresorcinol: CARN: 136-77-6). In addition, the fact that compounds of the Formula 1, and here in particular styrylresorcinol (Formula 4), have a more powerful tyrosinase-inhibiting activity compared with the known skin- and hair-lightening active compound kojic acid was particularly surprising, as a result of which they can be used in particularly low, and thus toxicologically and dermatologically acceptable, concentration in cosmetic products; styrylresorcinol has a tyrosinase-inhibiting action that is more powerful by a factor of approximately 215 than that of kojic acid.

The Applicant's activity studies with synthetic styrylresorcinol (Formula 4; CARN:85-27-8; 4-(1-phenylethyl)-1, 3-dihydroxybenzene) prepared in accordance with methods known from the literature confirm, for example, that the compounds of the Formula 1 (diphenylmethane derivatives) and also mixtures of substances that contain one or more compounds of the Formula 1, where the groups R1 to R5 in each case have the abovementioned meaning, have a powerful tyrosinase-inhibiting action and thus are outstandingly suitable for use as skin lightening agents and as agents for combating age spots. In this context, because of their high stability to light, they are outstandingly suitable for use as skin lighteners in cosmetic products and the like, as alternatives for or as supplements to known skin-lightening active compounds (such as, for example, hydroquinone, arbutin or ascorbic acid). The compound of the Formula 4 and the further compounds of the Formula 1, in which the OH groups are in the meta- or para-position with respect to one another, are, moreover, very stable to oxygen.

Tyrosinase inhibition usually takes place for cosmetic reasons, but in exceptional cases can also have a therapeutic character. Furthermore, the compounds of the Formula 1 can also be used in the food industry or in the aroma industry as browning-inhibiting additives; in this context see below.

The compounds of the Formula 1, in particular insofar as they are used as agents for skin and hair lightening or as agents for combating age spots, are as a rule applied topically in the form of solutions, creams, lotions, gels, sprays or the like.

Important fields of application in this context are cosmetic, in particular dermatological and/or keratinological formulations, which (apart from the presence of compounds of the Formula 1) are of customary composition, and serve for cosmetic, in particular dermatological and/or keratinological, sunscreening, for the treatment, the care and the cleansing of the skin and/or the hair or as a make-up product in decorative cosmetics. Correspondingly, such formulations, depending on their composition, can be used, for example, as skin protection cream, cleansing milk, cleansing soap, sunscreen lotion, nutrient cream, day cream or night cream, deodorant, antiperspirant, shampoo, hair care agent, hair conditioner or hair colourant and, in this context, are preferably in the form of an emulsion, lotion, milk, cream, hydrodispersion gel, balm, spray, foam, liquid soap, bar of soap, hair-(sic), roll-on, stick or make-up.

Furthermore, the diphenylmethane derivatives according to the invention can also be used in foods. Particularly preferred product categories here are in particular those foods that, because of their naturally occurring content of phenolic compounds, tend to spontaneous browning reactions under the influence of endogenous polyphenol oxidases when processing. These include, in particular, fruit and vegetable products, in particular apples, pears or potatoes, or crustaceans, such as, in particular, crabs, langustines or shrimps, in which context this list must, of course, not be regarded as complete and can be expanded as desired.

The concentration of the diphenylmethane derivatives of the Formula 1 in formulations (in particular formulations to be applied topically) is preferably in the range of 0.0001 to 20% (m/m), preferentially in the range of 0.001 to 5% (m/m) and particularly preferentially in the range of 0.01 to 1% (m/m). In these formulations the tyrosinase-inhibiting active compound can be used (a) prophylactically or (b) as needed.

The concentration of the amount of active compound that is, for example, to be applied daily differs and depends on the physiological condition of the test person and on parameters specific to the individual, such as age or body weight. Diphenylmethane derivatives of the Formula 1 can be used on their own, as mixtures or also in combination with further tyrosinase-inhibiting substances.

The compounds of the Formula 1 (where R1 to R5 have the meanings indicated above and what has been stated above also applies in respect of the preferred meanings of R1 to R5) can also be used as a constituent of cosmetic agents and fragrance compositions (perfume compositions) and, for example, can impart a tyrosinase-inhibiting action to a perfumed (for example cosmetic) end product. A particularly preferred fragrance composition comprises (a) a fragrance in an amount that has a sensory action, (b) one or more compounds of the Formula 1 (where R1 to R5 can have the meanings indicated above) in an amount that has a tyrosinase-inhibiting action and optionally (c) one or more excipients and/or additives. Since the perfume content in a cosmetic end product is frequently in the range of approximately 1% (m/m), a perfume which contains a compound of the Formula 1 will preferably consist to approximately 5 to 50% (m/m) of one or more compounds of the Formula 1. It has proved particularly advantageous that the substances of the Formula 1 have only a weak odour of their own, or are completely odourless since this property predestines them for use in a fragrance composition.

In a preferred method for cosmetic and/or therapeutic skin lightening and for the treatment (combating) of age spots, the concentration in which the synergistically active mixtures according to the invention is used is also in the range between 0.0001 to 20% (m/m), preferably in the range between 0.001 to 5% (m/m) and particularly preferentially in the range of 0.01 to 1% (m/m), in each case based on the total mass of the cosmetic or pharmaceutical product which contains the mixture.

In this context, the diphenylmethane derivatives of the Formula 1 can be used (a) prophylactically or (b) as needed.

It is pointed out that, in the context of the present text, the term diphenylmethane derivatives in the case of the derivatives of the Formula 1 that have differently substituted phenyl radicals and for which, at the same time, R2 and R3 differ, also comprises the pure S-configured enantiomers, the R-configured enantiomers and arbitrary mixtures of S- and R-configured enantiomers. It is true that for commercial reasons it is particularly advantageous in these cases to use mixtures of racemates of the particular diphenylmethane derivatives for skin lightening and/or for combating age spots since these mixtures are particularly easily accessible by synthesis; however, the pure enantiomers or non-racemic mixtures of these enantiomers are also suitable for the purposes according to the invention.

The diphenylmethane derivatives of the Formula 1 used according to the invention can be incorporated without difficulty in conventional cosmetic or dermatological formulations such as, inter alia, pump sprays, aerosol sprays, creams, ointments, tinctures, lotions, nail care products (for example nail varnishes, nail varnish removers, nail balsams) and the like. In this context it is also possible, and in some cases advantageous, to combine the diphenylmethane derivatives of the Formula 1 used according to the invention with further active compounds, for example with other substances that have a skin and hair lightening action or are active against age spots. In this context the cosmetic and/or dermatological/keratological formulations containing the diphenylmethane derivatives of the Formula 1 can otherwise be of customary composition and serve for treatment of the skin and/or the hair in the sense of a dermatological or keratological treatment or of a treatment in the sense of care cosmetics. However, they can also be used in make-up products in decorative cosmetics.

Cosmetic formulations that contain diphenylmethane derivatives of the Formula 1 can also contain further active compounds having a skin lightening action. In this context all skin lightening active compounds that are suitable or customary for cosmetic and/or dermatological applications can be used according to the invention. Advantageous skin lightening active compounds are, to this extent, kojic acid (5-hydroxy-2-hydroxymethyl-4-pyranone (sic), kojic acid derivatives such as, for example, kojic acid dipalmitate, arbutin, ascorbic acid, ascorbic acid derivatives, hydroquinone, hydroquinone derivatives, resorcinol, sulphur-containing molecules, such as, for example, glutathione or cysteine [lacuna] alpha-hydroxy acids (for example citric acid, lactic acid, malic acid) and the derivatives thereof, cycloalkanones, methylenedioxyphenyl alkanols, vinyl- and ethyl-gujacol (sic), inhibitors of the nitrogen oxide synthesis, such as, for example, L-nitroarginine and the derivatives thereof, 2,7-dinitroindazole or thiocitrulline, metal chelating agents (for example α-hydroxy fatty acids, palmitic acid, phytic acid, lactoferrin, humic acid, bile acid, bile extracts, bilirubin, biliverdin, EDTA, EGTA and derivatives thereof), flavonoids, retinoids, soya milk, serin protease inhibitors or lipoic acid or other synthetic or natural active compounds for skin and hair lightening, it being possible for the latter also to be used in the form of an extract from plants, such as, for example, bearberry extract, rice extract, liquorice root extract or constituents enriched therefrom, such as glabridin or licochalkon A, artocarpus extract, extract from Rumex and Ramulus species, extracts from pine species (Pinus) and extracts from Vitis species or stilbene derivatives enriched therefrom.

In numerous cases the diphenylmethane derivatives of the Formula 1 can be used in combination with preservatives. Preferably, preservatives such as benzoic acid, the esters and salts thereof, propionic acid and salts thereof, salicylic acid and salts thereof, 2,4-hexanoic acid (sorbic acid) and salts thereof, formaldehyde and paraformaldehyde, 2-hydroxybiphenyl ether and salts thereof, 2-zincsulphidopyridine-N-oxide, inorganic sulphites and bisulphites, sodium iodate, chlorobutanolum, 4-ethylmercury-(II)5-amino-1,3-bis(2-hydroxybenzoic (sic) acid, salts and esters thereof, dehydratcetic (sic) acid, formic acid, 1,6-bis(4-amidino-2-bromophenoxy)-n-hexane and salts thereof, the sodium salt of ethylmercury-(II)-thiosalicylic acid, phenylmercury and salts thereof, 10-undecylenic acid and salts thereof, 5-amino-1,3-bis(2-ethylhexyl)-5-methyl-hexahydropyrimidine, 5-bromo-5-nitro-1,3-dioxane, 2-bromo-2-nitro-1,3-propanediol, 2,4-dichlorobenzyl alcohol, N-(4-chlorophenyl)-N'-(3,4-dichlorophenyl)-urea, 4-chloro-m-cresol, 2,4,4'-trichloro-2'-hydroxy-diphenyl ether, 4-chloro-3,5-dimethylphenol, 1,1'-methylene-bis(3-(1-hydroxymethyl-2,4-dioximidazolidin-5-yl)urea), poly-(hexamethylene diguanide) hydrochloride, 2-phenoxyethanol, hexamethylentetramine, 1-(3-chloroallyl)-3,5,7-triaza-1-azonia-adamantane chloride, 1(4-chlorphenoxy)-1(1H-imidazol-1-yl)-

3,3-dimethyl-2-butanone, 1,3-bis-(hydroxy-methyl)-5,5-dimethyl-2,4-imidazolidinedione, benzyl alcohol, Octopirox, 1,2-dibromo-2,4-dicyanobutane, 2,2'-methylene-bis(6-bromo-4-chloro-phenol), bromo-chlorophene, mixture of 5-chloro-2-methyl-3(2H)-isothiazolinone and 2-methyl-3 (2H)isothiazlinone (sic) with magnesium chloride and magnesium nitrate, 2-benzyl-4-chlorophenol, 2-chloracetamide, chlorhexidine, chlorhexidine acetate, chlorhexidine gluconate, chlorhexidine hydrochloride, 1-phenoxy-propan-2-ol, N-alkyl($C_{12}$-$C_{22}$)trimethyl-ammonium bromide and chloride, 4,4-dimethyl-1,3-oxazolidine, N-hydroxymethyl-N-(1, 3-di(hydroxymethyl)-2,5-dioxoimidazolidin-4-yl)-N'-hydroxy-methyl urea, 1,6-bis(4-amidino-phenoxy)-n-hexane and salts thereof, glutaraldehyde 5-ethyl-1-aza-3,7-dioxabicyclo(3.3.0)octane, 3-(4-chlorphenoxy)-1,2-propanediol, hyamine, alkyl-($C_8$-$C_{18}$)-dimethyl-benzyl-ammonium chloride, alkyl-($C_8$-$C_{18}$)-dimethyl-benzyl ammonium bromide, alkyl-($C_8$-$C_{18}$)-dimethyl-benzylammonium saccharinate, benzyl-hemiformal, 3-iodo-2-propinyl-butyl carbamate, sodium hydroxymethyl-aminoacetate or sodium hydroxymethyl-aminoacetate (sic) are preferably chosen here.

In various cases it can also be advantageous to use the diphenylmethane derivatives of the Formula 1 in combination with substances that are used mainly for the inhibition of the growth of undesired microorganisms on or in animal organisms. In addition to conventional preservatives, further active compounds that are worthy of mention in this regard are, in addition to the large group of conventional antibiotics, in particular the products relevant for cosmetics, such as triclosan, climbazol, octoxyglycerol, Octopirox (1-hydroxy-4-methyl-6-(2,4,4-trimethylpentyl)-2(1H)-pyridone, 2-aminoethanol), chitosan, farnesol, glycerol monolaurate or combinations of the said substances, which, inter alia, are used against underarm odour, foot odour or dandruff.

In addition, the diphenylmethane derivatives of the Formula 1 can also be used particularly advantageously in combination with perspiration-inhibiting active compounds (antiperspirants) for controlling body odour. Perspiration-inhibiting active compounds used are, in particular, aluminium salts, such as aluminium chloride, aluminium chlorohydrate, nitrate, sulphate, acetate etc. In addition, however, the use of zinc, magnesium and zirconium compounds can also be advantageous. Essentially the aluminium salts and—to a somewhat lesser extent—aluminium/zirconium salt combinations have proved their worth for use in cosmetic and dermatological antiperspirants. The partially neutralised aluminium hydroxychlorides, which are thus better tolerated by the skin but are not quite as effective, are also worthy of mention. In addition to aluminium salts, further substances can also be used, such as, for example, a) protein-precipitating substances such as, inter alia, formaldehyde, glutaraldehyde, natural and synthetic tanning agents and also trichloroacetic acid, which give rise to surface closure of the sweat glands, b) local anaesthetics (inter alia dilute solutions of, for example, lidocaine, prilocaine or mixtures of such substances) that switch off the sympathetic supply of the sweat glands by blocking the peripheral nerve paths, c) zeolites of the X, A or Y type, which in addition to reducing sweat secretion also act as adsorbents for bad odours, and d) botulinus toxin (toxin of the bacterium *Chlostridium botulinum*), which is also used in the case of hyperhidrosis, a pathologically increased sweat secretion, and the action of which is based on an irreversible blockage of the release of the transmitter substance acetylcholine relevant for sweat secretion.

In some cases a combination with (metal) chelating agents can also be advantageous. In this context, (metal) chelating agents that are preferably to be used are, inter alia, α-hydroxy fatty acids, phytic acid, lactoferrin, α-hydroxy acids, such as, inter alia, citric acid, lactic acid and malic acid, as well as humic acids, bile acids, bile extracts, bilirubin, biliverdin or EDTA, EGTA and derivatives thereof.

For use, the cosmetic and/or dermatologically active diphenymethane derivatives of the Formula 1 are applied to the skin and/or the hair in an adequate amount in the manner customary for cosmetics and dermatological products. In this context cosmetic and dermatological formulations that contain a mixture according to the invention and additionally act as a sunscreen offer particular advantages. Advantageously, these formulations contain at least one UVA filter and/or at least one UVB filter and/or at least one inorganic pigment. In this context the formulations can be in various forms, such as are, for example, customarily employed for sunscreen formulations. Thus, they can be, for example, a solution, an emulsion of the water-in-oil (W/O) type or of the oil-in-water (O/W) type or a multiple emulsion, for example of the water-in-oil-in-water (W/O/N) type, a gel, a hydrodispersion, a solid stick or also an aerosol.

As mentioned, formulations that contain diphenylmethane derivatives of the Formula 1 can particularly advantageously be combined with substances that absorb UV radiation, the total amount of the filter substances being, for example, 0.01% (m/m) to 40% (m/m), preferably 0.1% to 10% (m/m), in particular 1.0 to 5.0% (m/m), based on the total weight of the formulations, in order to make available cosmetic formulations that protect the hair and/or the skin against ultraviolet radiation. Advantageously these formulations contain at least one UVA filter and/or at least one UVB filter and/or at least one inorganic pigment, so that a protection factor of at least >2 (preferably >5) is achieved. In this context, these formulations according to the invention can be in various forms, such as are customarily used, for example for sunscreen formulations. Thus, they can, for example, be a solution, an emulsion of the water-in-oil (W/O) type or of the oil-in-water (O/W) type or a multiple emulsion, for example of the water-in-oil-in-water (W/O/W) type, a gel, a hydrodispersion, a solid stick or also an aerosol.

If the formulations according to the invention contain UVB filter substances, these can be oil-soluble or water-soluble. Advantageous oil-soluble UVB filters are, for example: 3-benzylidenecamphor derivatives, preferably 3-(4-methylbenzylidene)camphor, 3-benzylidenecamphor; 4-aminobenzoic acid derivatives, preferably 2-ethylhexyl 4-(dimethylamino)-benzoate, amyl 4-(dimethylamino)benzoate, esters of cinnamic acid, preferably 2-ethylhexyl 4-methoxycinnamate, isopentyl 4-methoxycinnamate; esters of salicylic acid, preferably 2-ethylhexyl salicylate, 4-isopropylbenzyl salicylate, homomenthyl salicylate, derivatives of benzophenone, preferably 2-hydroxy-4-methoxybenzophenone, 2-hydroxy-4-methoxy-4'-methylbenzophenone, 2,2'-dihydroxy-4-methoxybenzophenone, esters of benzmalonic acid, preferably di(2-ethylhexyl) 4-methoxybenzalmalonate, 2,4,6-trianilino-(p-carbo-2'-ethyl-1'-hexyloxy)-1,3,5-triazine.

Advantageous water-soluble UVB filters are, for example, salts of 2-phenylbenzimidazole-5-sulphonic acid, such as the sodium, potassium or triethanolammonium salt thereof, and also the sulphonic acid itself; sulphonic acid derivatives of benzophenones, preferably 2-hydroxy-4-methoxybenzo-phenone-5-sulphonic acid and salts thereof; sulphonic acid derivatives of 3-benzylidenecamphor, such as, for example, 4-(2-oxo-3-bornylidenemethyl)benzenesulphonic acid, 2-methyl-5-(2-oxo-3-bornylidene-methyl)sulphonic acid and salts thereof and also 1,4-di(2-oxo-10-sulpho-3-bornylidenemethyl)-benzene and salts thereof (the corresponding 10-sulphato compounds, for example the corresponding sodium, potassium or triethanolammonium salt) and also benzene-1,4-di(2-oxo-3-bornylidenemethyl-10-sulphonic acid (sic).

The above list of the said UVB filters that can be used in combination with the diphenylmethane derivatives of the Formula 1 should, of course, not be understood as definitive. It can also be advantageous to employ UVA filters, such as are customarily contained in cosmetic formulations. These substances are preferably derivatives of dibenzoylmethane, in particular 1-(4'-tert.-butylphenyl)-3-(4'-methoxyphenyl)-propane-1,3-dione and 1-phenyl-3-(4'-isopropylphenyl)propane-1,3-dione.

In cosmetic formulations, the diphenylmethane derivatives of the Formula 1 can advantageously be combined with cosmetic auxiliaries, such as are customarily used in such formulations, thus, for example, with: antioxidants; perfume oils; agents to prevent foaming; colourants; pigments that have a colouring action; thickeners; surface-active substances; emulsifiers; plasticizing substances; moistening and/or moisture-retaining substances; fats, oils, waxes; other conventional constituents of a cosmetic formulation, such as alcohols, polyols, polymers, foam stabilisers; electrolytes, organic solvents or silicone derivatives.

A high content of treatment substances is usually advantageous in formulations containing diphenylmethane derivatives of the Formula 1 for the topical prophylactic or cosmetic treatment of the skin. According to a preferred embodiment, the compositions contain one or more animal and/or vegetable treatment fats and oils, such as olive oil, sunflower oil, purified soya oil, palm oil, sesame oil, rapeseed oil, almond oil, borage oil, evening primrose oil, coconut oil, shea butter, jojoba oil, sperm oil, beef tallow, neatsfood oil and lard, and also optionally further treatment constituents, such as, for example, fatty alcohols having 8-30 C atoms. Here the fatty alcohols can be saturated or unsaturated and straight-chain or branched. For example, decanol, decenol, octanol, octenol, dodecanol, dodecenol, octadienol, decadienol, dodecadienol, oleyl alcohol, ricinol (sic) alcohol, erucic alcohol, stearyl alcohol, isostearyl alcohol, cetyl alcohol, lauryl alcohol, myristyl alcohol, arachidyl alcohol, capryl alcohol, capric alcohol, linoleyl alcohol, linolenyl alcohol and behenyl alcohol, as well the guerbet alcohols thereof can be used, in which context it would be possible to extend the list virtually arbitrarily by further structurally chemically related alcohols. The fatty alcohols preferably originate from natural fatty acids, and usually are prepared from the corresponding esters of the fatty acids by reduction. Furthermore, fatty alcohol fractions that are formed from naturally occurring fats and fat oils by reduction, such as, for example, beef tallow, peanut oil, colza oil, cottonseed oil, soya oil, sunflower oil, palm kernel oil, linseed oil, maize oil, castor oil, rapeseed oil, sesame oil, cocoa butter and cocoa fat, can be used.

In addition, the treatment substances that can preferably be combined with the diphenylmethane derivatives of the Formula 1 also include
  ceramides, ceramides being understood to be N-acyl-sphingosines (fatty acid amides of sphingosine) or synthetic analogues of such lipids (so-called pseudoceramides), which clearly improve the water retention capacity of the stratum corneum.
  phospholipids, for example soya lecithin, egg lecithin and cephalins vaseline, paraffin and silicone oils; the latter include, inter alia, dialkyl- and alkylaryl-siloxanes, such as dimethylpolysiloxane and methylphenylpolysiloxane, as well as the alkoxylated and quaternised derivatives thereof.

Animal and/or vegetable hydrolysed proteins can advantageously also be added to the diphenylmethane derivatives of the Formula 1. In this regard, in particular elastin, collagen, keratin, lactoprotein, soya protein, oat protein, pea protein, almond protein and wheat protein fractions or corresponding hydrolysed proteins, but also the condensation products thereof with fatty acids, and also quaternised hydrolysed proteins are advantageous, the use of vegetable hydrolysed proteins being preferred.

Insofar as a cosmetic or dermatological formulation containing diphenylmethane derivatives of the Formula 1 is a solution or lotion, the solvents used can advantageously be:
  water or aqueous solutions;
  fatty oils, fats, waxes and other natural and synthetic fatty bodies, preferably esters of fatty acids with alcohols having a low C number, for example with isopropanol, propylene glycol or glycerol, or esters of fatty alcohols with alkanoic acids having a low C number or with fatty acids;
  alcohols, diols or polyols having a low C number, as well as the ethers thereof, preferably ethanol, isopropanol, propylene glycol, glycerol, ethylene glycol, ethylene glycol monoethyl or monobutyl ether, propylene glycol-monomethyl, monoethyl or monobutyl ether, diethylene glycol monomethyl or monoethyl ether and analogous products. In particular, mixtures of the abovementioned solvents are used.

In the case of alcoholic solvents, water can be a further constituent.

Cosmetic formulations that contain diphenylmethane derivatives of the Formula 1 can also contain antioxidants, it being possible to use all antioxidants suitable or customary for cosmetic and/or dermatological applications. Advantageously, the antioxidants are selected from the group consisting of amino acids (for example glycine, histidine, tyrosine, tryptophan) and the derivatives thereof, imidazoles (for example urocanic acid) and the derivatives thereof, peptides such as D, L-carnosine, D-carnosine, L-carnosine and the derivatives thereof (for example anserine), carotinoids, carotenes (for example $\alpha$-carotene, $\beta$-carotene, lycopene) and the derivatives thereof, lipoic acid and the derivatives therefore (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl lauryl (sic), palmitoyl, oleyl, 7-linoleyl, cholesteryl and glyceryl esters thereof) as well as the salts thereof, dilauryl thiodipropionate, distearyl thiodipropionate, thiodipropionic acid and the derivatives thereof (esters, ethers, peptides, lipids, nucleotides, nucleosides and salts) and also sulphoximine compounds (for example buthionine sulphoximines, homocysteine sulphoximine, buthionine sulphones, penta-, hexa-, hepta-thionine suphoximine) in very low tolerated doses, and also (metal) chelating agents, for example $\alpha$-hydroxy fatty acids, palmitic acid, phytic acid, lactoferrin, $\alpha$-hydroxy acids (for example citric acid, lactic acid, malic acid), humic acid, bile acid, bile extracts, bilirubin, biliverdin, EDTA, EGTA and the derivatives thereof, unsaturated fatty acids and the derivatives thereof (for example $\gamma$-linolenic acid, linoleic acid, oleic acid), folic acid and the derivatives thereof, ubiquinone and ubiquinol and the derivatives thereof, Vitamin C and derivatives (for example ascorbyl palmitate, Mg ascorbyl phosphate, ascorbyl acetate), tocopherols and the derivatives thereof (for example vitamin Vitamin E acetate (sic)), Vitamin A and the derivatives thereof (Vitamin A palmitate) and also coniferyl benzoate of benzoin resin, rutinic acid and the derivatives thereof, ferrulic acid and the derivatives thereof, butylhydroxytoluene, butylhydroxyanisole, nordihydroguaiacic acid, nordihydroguaiaretic acid, trihydroxybutyrophenone, uric acid and the derivatives thereof, mannose and the derivatives thereof, zinc and the derivatives thereof (for example ZnO, ZnSO4 (sic)), selenium and the derivatives thereof (for example selenium methionine), stilbenes and the derivatives thereof (for example stilbene oxide, trans-stilbene oxide) and also derivatives (salts, esters, ethers, sugars, nucleotides, nucleosides, peptides and lipids) of the said active compounds.

Cosmetic formulations that contain diphenylmethane derivatives of the Formula 1 can advantageously also contain vitamins and vitamin precursors, it being possible to use all vitamins and vitamin precursors suitable or customary for cosmetic and/or dermatological applications. Mention may be made here in particular of vitamins and vitamin precursors such as tocopherols, Vitamin A, nicotinic acid and nicotinomide, further vitamins of the B complex, in particular biotin, and Vitamin C, pantothenyl alcohol and the derivatives thereof, in particular esters and ethers of pantothenyl alcohol, and also derivatives of pantothenyl alcohols obtained cationically, such as, for example, pantothenyl alcohol triacetate, pantothenyl alcohol, monoethyl ether and the mono acetate thereof and also cationic pantothenyl alcohol derivatives.

Cosmetic formulations, which advantageously contain diphenylmethane derivatives of the Formula 1, can also contain anti-inflammatory active compounds and/or active compounds that alleviate reddening and/or itching. In this context all anti-inflammatory active compounds and active compounds that alleviate reddening and/or itching that are suitable or customary for cosmetic and/or dermatological applications can be used. Advantageously, the anti-inflammatory active compounds and active compounds alleviating reddening and/or itching that are used are steroidal anti-inflammatory substances of the corticosteroid type, such as, for example, hydrocortisone, dexamethasone, dexamethasone phosphate, methylprednisolone or cortisone, it being possible to expand the list by adding further steroidal anti-inflammatory agents. Non-steroidal anti-inflammatory agents can also be used. Oxicams, such as piroxicam or tenoxicam; salicylates, such as aspirin, Disalcid, Solprin or fendosal; acetic acid derivatives, such as diclofenac, fenclofenac, indomethacin, sulindac, tolmetin, or clindanac; fenamates, such as mefenamic, meclofenamic, flufenamic or niflumic; propionic acid derivatives, such as ibuprofen, naproxen, benoxaprofen or pyrazoles, such as phenylbutazone, oxyphenylbutazone, febrazone or azapropazone, may be mentioned here by way of example. Alternatively, natural anti-inflammatory substances and substances that alleviate reddening and/or itching can be used. Plant extracts, special highly active plant extract fractions and also highly pure active substances isolated from plant extracts can be used. Extracts, fractions and active substances from camomile, aloe vera, Commiphora species, Rubia species, willows, willow-herb, oats and pure substances such as, inter alia, bisabolol, apigenin-7-glucoside, boswellic acid, phytosterols, glycyrrhizine, glabridin or licochalkon A are particularly preferred. The formulations containing diphenylmethane derivatives of the Formula 1 can also contain mixtures of two or more anti-inflammatory active compounds.

Bisabolol, boswellic acid and extracts and isolated highly pure active compounds from oats and Echinacea are particularly preferred for use in the sense of the invention; α-Bisabolol and extracts and isolated highly pure active compounds from oats are particularly preferred.

The amount of the anti-irritants (one or more compounds) in the formulations is preferably 0.0001 to 20% (m/m), particularly preferentially 0.0001-10% (m/m), in particular 0.001-5% (m/m), based on the total weight of the formulation.

Cosmetic formulations that contain diphenylmethane derivatives of the Formula 1 can advantageously also contain moisturisers. Moisturisers used are, for example, the following substances: sodium lactate, urea, alcohols, sorbitol, glycerol, propylene glycol, collagen, elastin or hyaluronic acid, diacyl adipates, petroleum jelly, ectoin, urocanic acid, lecithin, pantheol, phytanetriol, lycopene, algae extract, ceramides, cholesterol, glycolipids, chitosan, chondroitin sulphate, polyamino acids and sugars, lanolin, lanolin esters, amino acids, alpha-hydroxy acids (for example, citric acid, lactic acid, malic acid) and the derivatives thereof, sugars (for example inositol), alpha-hydroxy fatty acids, phytosterols, triterpene acids, such as betulinic acid or ursolic acid, algae extracts.

Cosmetic formulations that contain diphenylmethane derivatives of the Formula 1 can advantageously also contain mono- di- and oligo-saccharides, such as, for example, glucose, galactose, fructose, mannose, fructose (sic) and lactose.

Cosmetic formulations that contain diphenylmethane derivatives of the Formula 1 can advantageously also contain plant extracts, which are usually prepared by extraction of the complete plant, but in individual cases are also prepared exclusively from blossom and/or leaves, wood, bark or roots of the plant. With regard to the plant extracts that can be used, reference is made in particular to the extracts that are listed in the table starting on page 44 of the third edition of the Leitfaden zur Inhaltsstoffdeklaration kosmetischer Mittel, (Guide to the Declaration of Constituents of Cosmetic Agents), published by the Industrieverband Körperpflegemittel und Waschmittel e.V. (IKW), Frankfurt. The extracts from aloe, Hamamelis, algae, oak bark, willowherb, stinging nettles, dead nettles, hops, camomile, milfoil, arnica, calendula, burdock root, horse-tail, hawthorn, linden blossom, almonds, pine needles, horsechestnut, sandalwood, juniper, coconut, mango, apricot, orange, lemon, lime, grapefruit, apple, green tea, grapefruit seed, wheat, oats, barley, sage, thyme, basil, rosemary, birch, mallow, bittercrass, willow bark, restharrow, coltsfoot, althaea, ginseng and ginger root are particularly advantageous. Amongst these, the extracts from aloe vera, camomile, algae, rosemary. calendula, ginseng, cucumber, sage, stinging nettles, linden blossom, arnica and Hamamelis are particularly preferred. Mixtures of two or more plant extracts can also be employed. Extraction agents that can be used for the preparation of the said plant extracts can be, inter alia, water, alcohols and mixtures thereof. Amongst the alcohols, lower alcohols, such as ethanol and isopropanol, but also polyhydric alcohols, such as ethylene glycol, propylene glycol and butylene glycol are preferred in this context, and specifically both as sole extracting agent and also in mixtures with water. The plant extracts can be used in the pure form or also in dilute form.

Cosmetic formulations that contain diphenylmethane derivatives of the Formula 1 can also contain anionic, cationic, non-ionic and/or amphoteric surfactants, especially if crystalline or microcrystalline solids, for example inorganic micropigments, are to be incorporated into the formulations. Surfactants are amphiphilic subs stances that are able to dissolve organic, non-polar substances in water. In this context the hydrophilic parts of a surfactant molecule are usually polar functional groups, for example, $—COO^-$, $—OSO_3^{2-}$, $—SO_3^-$, whilst the hydrophobic parts are as a rule non-polar hydrocarbon radicals. Surfactants are generally classified according to the nature and charge of the hydrophilic part of the molecule. Four groups can be differentiated here:

anionic surfactants,
cationic surfactants,
amphoteric surfactants and
non-ionic surfactants.

Anionic surfactants usually contain carboxylate, sulphate or sulphonate groups as functional groups. In aqueous solution they form negatively charged organic ions in the acid or neutral medium. Cationic surfactants are characterised virtually exclusively by the presence of a quaternary ammonium group. In aqueous solution they form positively charged organic ions in the acid or neutral medium. Amphoteric surfactants contain both anionic and cationic groups and accordingly behave like anionic or cationic surfactants in aqueous solutions, depending on the pH value. They have a positive charge in a strongly acid medium and a negative charge in an alkaline medium. In the neutral pH range, on the other hand, they are zwitter ionic. Polyether chains are typical of non-ionic surfactants. Non-ionic surfactants do not form ions in an aqueous medium.

A. Anionic Surfactants

Anionic surfactants that can advantageously be used are acylamino acids (and the salts thereof), such as acylglutamates, for example, sodium acylgultamate, di-TEA-palmitoyl aspartate and sodium capryl/caprin glutamate, acylpeptides, for example, palmitoyl-hydrolysed lactoprotein, sodium cocoyl-hydrolysed soya protein and sodium/potassium cocoyl-hydrolysed collagen, sarcosinates, for example, myristoyl sarcosine, TEA lauroyl sarcosinate, sodium lauroyl sarcosinate and sodium cocoyl sarcosinate, taurates, for example, sodium lauroyl taurate and sodium methylcocoyl taurate, acyl lactylates, lauroyl lactylate, caproyl lactylate alaninates carboxylic acids and derivatives, such as, for example, lauric acid, aluminium stearate, magnesium alkanolate and zinc undecylenate, ester-carboxylic acids, for example calcium stearoyl lactylate, laureth-6 citrate and sodium PEG-4 lauramidocarboxylate, ether-carboxylic acids, for example sodium laureth-13 carboxylate and sodium PEG-6 cocamide carboxylate, phosphoric acid esters and salts, such as, for example, DEA-oleth-10 phosphate and dilaureth-4 phosphate, sulphonic acids and salts, such as acyl isothionates, for example sodium/ammonium cocoyl-isethionate, alkylarylsulphonates, alkylsulphonates, for example sodium coconut monoglyceride sulphate, sodium $C_{12-14}$ olefin-sulphonate sodium lauryl sulphoacetate and magnesium PEG-3 cocamido-sulphate, sulphosuccinates, for example, dioctylsodium sulphosuccinate, disodium laureth-sulphosuccinate, disodium laurylsulphosuccinate and disodium undecylenamido MEA-sulphosuccinate and sulphuric acid esters, such as alkyl ether sulphate, for example, sodium, ammonium, magnesium, MIPA, TIPA laureth sulphate, sodium myreth sulphate and sodium C12-13 pareth sulphate, alkyl sulphates, for example, sodium, ammonium and TEA lauryl sulphate.

B. Cationic Surfactants

Cationic surfactants that can advantageously be used are
alkylamines,
alkylimidazoles,
ethoxylated amines and
quaternary surfactants

$RNH_2CH_2CH_2COO^-$ (at pH=7)

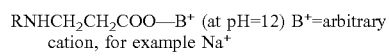

$RNHCH_2CH_2COO—B^+$ (at pH=12) $B^+$=arbitrary cation, for example $Na^+$ esterquats Quaternary surfactants contain at least one N atom that is covalently bonded to 4 alkyl or aryl groups. This leads to a positive charge, irrespective of the pH value. Alkylbetaine, alkylamidopropylbetaine and alkylamidopropyl-hydroxysulfaine are advantageous. The cationic surfactants used can furthermore preferably be chosen from the group comprising the quaternary ammonium compounds, in particular benzyltrialkyl-ammonium chloride or bromide, such as, for example, benzyldimethylstearyl-ammonium chloride, and also alkyltrialkylammonium salts, for example cetyltrimethylammonium chloride or bromide, alkyldimethylhydroxyethylammonium chlorides or bromides, dialkyldimethylammonium chlorides or bromides, alkylamidoethyl-trimethyl-ammonium ether sulphates, alkylpyridinium salts, for example lauryl- or cetyl-pyrimidinium chloride, imidazoline derivatives and compounds of a cationic nature, such as amine oxides, for example alkyldimethylamine oxides or alkylaminoethyldimethylamine oxides. Cetyltrimethyl-ammonium salts can be used particularly advantageously.

C. Amphoteric Surfactants

Amphoteric surfactants that can advantageously be used are acyl-/dialkylethylenediamine, for example sodium acylamphoacetate, disodium acylamphodipropionate, disodium alkylamphodiacetate, sodium acyl-amphohydroxy-propylsulphonate, disodium acylampho-diacetate and sodium acylamphopropionate, N-alkylamino acids, for example aminopropylalkylglutamide, alkylamino-propionic acid, sodium alkylimidodipropionate and lauroamphocarboxyglycinate.

D. Non-Ionic Surfactants

Non-ionic surfactants that can advantageously be used are
alcohols,
alkanolamides, such as cocamides MEA/DEA/MIPA,
amine oxides, such as cocoamidopropylamine oxide,
esters, that are formed by esterification of carboxylic acids with ethylene oxide, glycerol, sorbitan or other alcohols,
ethers, for example ethoxylated/propoxylated alcohols, ethoxylated/propoxylated esters, ethoxylated/propoxylated glycerol esters, ethoxylated/propoxylated cholesterols, ethoxylated/propoxylated triglyceride esters, ethoxylated [lacuna] propoxylated lanolin, ethoxylated/propoxylated polysiloxanes, propoxylated POE ethers and alkylpolyglycosides, such as lauryl glucoside, decyl glycoside and coco glycoside.
sucrose esters and ethers
polyglycerol esters, diglycerol esters, monoglycerol esters
methylglucose esters, ester of hydroxy acids The use of a combination of anionic and/or amphoteric surfactants with one or more non-ionic surfactants is also advantageous.

The surface-active substance can be present in a concentration of between 1 and 98% (m/m) in the formulations according to the invention containing diphenylmethane derivatives of the Formula 1, based on the total weight of the formulations.

Cosmetic or dermatological formulations that contain diphenylmethane derivatives of the Formula 1 according to the invention can also be in the form of emulsions.

The oil phase can advantageously be chosen from the following group of substances:
  mineral oils, mineral waxes
  fatty oils, fats, waxes and other natural and synthetic fatty bodies, preferably esters of fatty acids with alcohols having a low C number, for example with isopropanol, propylene glycol or glycerol, or esters of fatty alcohols with alkanoic acids having a low C number or with fatty acids;
  alkyl benzoates;
  silicone oils, such as dimethylpolysiloxanes, diethylpolysiloxanes, diphenylpolysiloxanes and mixed forms therefrom.

Advantageously, (a) esters of saturated and/or unsaturated, branched and/or straight-chain alkanecarboxylic acids having a chain length of 3 to 30 C atoms and saturated and/or unsaturated, branched and/or straight-chain alcohols having a chain length of 3 to 30 C atoms, (b) esters of aromatic carboxylic acids and saturated and/or unsaturated, branched and/or straight-chain alcohols having a chain length of 3 to 30 C atoms can be used. Preferred ester oils are isopropyl myristate, isopropyl palmitate, isopropyl stearate, isopropyl oleate, n-butyl stearate, n-hexyl-laurate, n-decyl oleate, isooctyl stearate, isononyl stearate, isononyl isononanoate, 2-ethylhexyl palmitate, 2-ethylhexyl laurate, 2-hexyldecyl stearate, 2-octyidodecyl-palmitate, oleyl oleate, oleyl erucate, erucyl oleate, erucyl erucate and synthetic, semi-synthetic and natural mixtures of such esters, for example, jojoba oil.

Furthermore, the oil phase can advangaeously be chosen from the group comprising the branched and straight-chain hydrocarbons and waxes, the silicone oils, the dialkyl ethers, the group comprising the saturated or unsaturated, branched or straight-chain alcohols, and also the fatty acid triglycerides, specifically, the triglycerol esters of saturated and/or unsaturated, branched and/or straight-chain alkanecarboxylic acids having a chain length of 8 to 24, in particular 12 to 18 C atoms. The fatty acid triglycerides can advantageously be chosen from the group comprising the synthetic, semi-synthetic and natural oils, for example, olive oil, sunflower oil, soya oil, peanut oil, rapeseed oil, almond oil, palm oil, coconut oil, palm kernel oil and more of the like. Arbitrary admixtures of such oil and wax components can also advantageously be used. In some cases it is also advantageous to use waxes, for example cetyl palmitate, as the sole lipid component of the oil phase; advantageously, the oil phase is chosen from the group that consists of 2-ethylhexyl isostearate, octyldodecanol, isotridecyl isononanoate, isoeicosane, 2-ethylhexyl cocoate, $C_{12-15}$-alkyl benzoate, capryl-capric acid triglyceride and dicaprylyl ether. Mixtures of $C_{12-15}$-alkyl benzoate and 2-ethylhexyl isostearate, mixtures of $C_{12-15}$-alkyl benzoate and isotridecyl isononanoate and mixtures of $C_{12-15}$-alkyl benzoate, 2-ethylhexyl isostearate and isotridecyl isononanoate are particularly advantageous. The hydrocarbons paraffin oil, squalane and squalene can also advantageously be used.

Advantageously, the oil phase can furthermore contain cyclic or linear silicone oils or consist entirely of such oils, it being, however, preferred to use an additional content of other oil phase components in addition to the silicone oil or the silicone oils. Cyclomethicone (for example, decamethylcyclopentasiloxane) can advantageously be used as silicone oil. However, other silicone oils can also advantageously be used, for example undecamethylcyclotrisiloxane, polydimethylsiloxane and poly(methyl-phenylsiloxane). Furthermore, mixtures of cyclomethicone and isotridecyl isononanoate and of cyclomethicone and 2-ethylhexyl isostearate are particularly advantageous.

The aqueous phase of formulations that contain diphenylmethane derivatives of the Formula 1 and are in the form of an emulsion can advantageously comprise: alcohols, diols or polyols having a low C number and also the ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and also alcohols having a low C number, for example, ethanol, isopropanol, 1,2-propanediol, glycerol and also, in particular, one or more thickeners, which thickener or thickeners can advantageously be chosen from the group comprising silicon dioxide, aluminium silicates, polysaccharides and the derivatives thereof, for example hyaluronic acid, xanthan gum, hydroxypropyl-methylcellulose, and particularly advantageously from the group comprising the polyacrylates, preferably a polyacrylate from the group comprising the so-called carbopols, for example carbopols of types 980, 981, 1382, 2984, 5984, in each case on their own or in combination.

Formulations that contain diphenylmethane derivatives of the Formula 1 according to the invention and are in the form of an emulsion advantageously contain one or more emulsifiers. O/W emulsifiers can, for example, advantageously be chosen from the group comprising the polyethoxylated or polypropoxylated or polyethoxylated and polypropoxylated products, for example:
  the fatty alcohol ethoxylates
  the ethoxylated wool wax alcohols,
  the polyethylene glycol ethers of the general formula
    R—O—(—CH$_2$—CH$_2$—O—)$_n$—R',
  the fatty acid ethoxylates of the general formula
    R—COO—(—CH$_2$—CH$_2$—O—)$_n$—H,
  the etherified fatty acid ethoxylates of the general formula

R—COO—(—CH$_2$—CH$_2$—O—)—R', the esterified fatty acid ethoxylates of the general formula R—COO—(—CH$_2$—CH$_2$—O—)$_n$—C(O)—R', the polyethylene glycol glycerol fatty acid esters
  the ethoxylated sorbitan esters
  the cholesterol ethoxylates
  the ethoxylated triglycerides
  the alkyl ether carboxylic acids of the general formula R—COO—(—CH$_2$—CH$_2$—O—)$_n$—OOH, and $n$ represent (sic) a number from 5 to 30, the polyoxyethylene sorbitol fatty acid esters,
  the alkyl ether sulphates of the general formula R—O—(—CH$_2$—CH$_2$—O—)$_n$—SO$_3$—H
  the fatty alcohol propoxylates of the general formula R—O—(—CH$_2$—CH(CH$_3$)—O—)$_n$—H the polypropylene glycol ethers of the general formula R—O—(—CH$_2$—CH(CH$_3$)—O—)$_n$—R' the propoxylated wool wax alcohols,
the esterified fatty acid propoxylates R—COO—(—CH$_2$—CH(CH$_3$)—O—)$_n$—R'
the esterified fatty acid propoxylates of the general formula R—COO—(—CH$_2$—CH(CH$_3$)—O—)$_n$—C(O)—R' the fatty acid propoxylates of the general formula

R—COO—(—CH$_2$—CH(CH$_3$)—O—)$_n$—H, the polypropylene glycol glycerol fatty acid esters
the propoxylated sorbitan esters
the cholesterol propoxylates
the propoxylated triglycerides
the alkyl ether carboxylic acids of the general formula R—O—(—CH$_2$—CH(CH$_3$)—O—)$_n$—CH$_2$—COOH, the alkyl ether sulphates and the acids on which these sulphates are based of the general formula R—O—(—CH$_2$—CH(CH$_3$)—O—)$_n$—SO$_3$—H, the fatty alcohol ethoxylates/propoxylates of the general formula R—O—X$_n$—Y$_m$—H the polypropylene glycol ethers of the general formula R—O—X$_n$—Y$_m$—R'
the esterified fatty acid propoxylates of the general formula R—COO—X$_n$—Y$_m$—R'
the fatty acid ethoxylates/propoxylates of the general formula R—COO—X$_n$—Y$_m$—H.

According to the invention, the polyethoxylated or polypropoxylated or polyethoxylated and polypropoxylated O/W emulsifiers used are particularly advantageously chosen from the group comprising substances having HLB values of 11-18, very particularly advantageously having HLB values of 14.5-15.5, insofar as the O/W emulsifiers contain saturated radicals R and R'. If the O/W emulsifiers contain unsaturated radicals R and/or R', or if there are isoalkyl derivatives, the preferred HLB value of such emulsifiers can also be lower or higher.

It is advantageous to choose the fatty alcohol ethoxylates from the group comprising the ethoxylated stearyl alcohols, cetyl alcohols, cetylstearyl alcohols (cetearyl alcohols). The following are particularly preferred:

Polyethylene glycol(13) stearyl ether (Steareth-13), polyethylene glycol(14) stearyl ether (Steareth-14), polyethylene glycol(15) stearyl ether (Steareth-15), polyethylene glycol(16) stearyl ether (Steareth-16), polyethylene glycol(17) stearyl ether (Steareth-17), polyethylene glycol(18) stearyl ether (Steareth-18), polyethylene glycol(19) stearyl ether (Steareth-19), polyethylene glycol(20) stearyl ether (Steareth-20), polyethylene glycol(12) isostearyl ether (Isosteareth-12), polyethylene glycol(13) isostearyl ether (Isosteareth-13), polyethylene glycol(14) isostearyl ether (Isosteareth-14), polyethylene glycol(15) isostearyl ether (Isosteareth-15), polyethylene glycol(16) isostearyl ether (Isosteareth-16), polyethylene glycol(17) isostearyl ether (Isosteareth-17), polyethylene glycol(18) isostearyl ether (Isosteareth-18), polyethylene glycol(19) isostearyl ether (Isosteareth-19), polyethylene glycol(20) isostearyl ether (Isosteareth-20), polyethylene glycol(13) cetyl-ether (Ceteth-13), polyethylene glycol(14) cetyl ether (Ceteth-14), polyethylene glycol(15) cetyl ether (Ceteth-15), polyethylene glycol(16) cetyl ether (Ceteth-16), polyethylene glycol(17) cetyl ether (Ceteth-17), polyethylene glycol(18) cetyl ether (Ceteth-18), polyethylene glycol(19) cetyl ether (Ceteth-19), polyethylene glycol(20) cetyl ether (Ceteth-20), polyethylene glycol(13) isocetyl ether (Isoceteth-13), polyethylene glycol(14) isocetyl ether (Isoceteth-14), polyethylene glycol(15) isocetyl ether (Isoceteth-15), polyethylene glycol(16) isocetyl ether (Isoceteth-16), polyethylene glycol(17) isocetyl ether (Isoceteth-17), polyethylene glycol(18) isocetyl-ether (Isoceteth-18), polyethylene glycol(19) isocetyl ether (Isoceteth-19), polyethylene glycol(20) isocetyl ether (Isoceteth-20), polyethylene glycol(12) oleyl ether (Oleth-12), polyethylene glycol(13) oleyl ether (Oleth-13), polyethylene glycol(14)-oleyl ether (Oleth-14), polyethylene glycol(15)oleyl ether (Oleth-15), polyethylene glycol(12) lauryl ether (Laureth-12), polyethylene glycol(12) isolauryl ether (Iso-laureth12), polyethylene glycol(13) cetyl stearyl ether (Ceteareth-13), polyethylene glycol(14) cetyl stearyl ether (Ceteareth-14), polyethylene glycol(15) cetyl stearyl ether (Ceteareth-15), polyethylene glycol(16) cetyl stearyl ether (Ceteareth-16), polyethylene glycol(17) cetyl stearyl ether (Ceteareth-17), polyethylene glycol(18) cetyl stearyl ether (Ceteareth-18), polyethylene glycol(19) cetyl stearyl ether (Ceteareth-19), polyethylene glycol(20) cetyl stearyl ether (Ceteareth-20).

It is furthermore advantageous to choose the fatty acid ethoxylates from the following group:

Polyethylene glycol(20) stearate, polyethylene glycol(21) stearate, polyethylene glycol(22) stearate, polyethylene glycol(23) stearate, polyethylene glycol(24) stearate, polyethylene glycol(25) stearate, polyethylene glycol(12) isostearate, polyethylene glycol(13) isostearate, polyethylene glycol(14) isostearate, polyethylene glycol(15) isostearate, polyethylene glycol(16) isostearate, polyethylene glycol(17) isostearate, polyethylene glycol(18) isostearate, polyethylene glycol(19) isostearate, polyethylene glycol(20) isostearate, polyethylene glycol(21) isostearate, polyethylene glycol(22) isostearate, polyethylene glycol(23) isostearate, polyethylene glycol(24) isostearate, polyethylene glycol(25) isostearate, polyethylene glycol(12) oleate, polyethylene glycol(13) oleate, polyethylene glycol(14) oleate, polyethylene glycol(15) oleate, polyethylene glycol(16) oleate, polyethylene glycol(17) oleate, polyethylene glycol(18) oleate, polyethylene glycol(19) oleate, polyethylene glycol(20) oleate.

Advantageously, sodium laureth-11-carboxylate can be used as ethoxylated alkyl ether carboxylic acid or the salt thereof. Sodium laureth 1-4 sulphate can advantageously be used as alkyl ether sulphate. Polyethylene glycol(30) cholesteryl ether can advantageously be used as ethoxylated cholesterol derivative. Polyethylene glycol(25) soyasterol has also proved useful.

The polyethylene glycol(60) evening primrose glycerides can advantageously be used as ethoxylated triglycerides.

It is furthermore advantageous to choose the polyethylene glycol glycerol fatty acid esters from the group comprising polyethylene glycol(20) glyceryl laurate, polyethylene glycol(21) glyceryl laurate, polyethylene glycol(22) glyceryl laurate, polyethylene glycol(23) glyceryl laurate, polyethylene glycol(6) glyceryl caprate/caprinate, polyethylene glycol(20) glyceryl oleate, polyethylene glycol(20) glyceryl isostearate, polyethylene glycol(18) glyceryl oleate/cocoate.

It is also advantageous to choose the sorbitan esters from the group comprising polyethylene glycol(20) sorbitan monolaurate, polyethylene glycol(20) sorbitan monostearate, polyethylene glycol(20) sorbitan monoisostearate, polyethylene glycol(20) sorbitan monopalmitate, polyethylene glycol(20) sorbitan monooleate.

The following can be used as advantageous W/O emulsifiers: fatty alcohols having 8 to 30 carbon atoms, monoglycerol esters of saturated and/or unsaturated, branched and/or straight-chain alkanecarboxylic acids having a chain length of 8 to 24, in particular 12 to 18 C atoms, diglycerol esters of saturated and/or unsaturated, branched and/or straight-chain alkanecarboxylic acids having a chain length of 8 to 24, in particular 12 to 18 C atoms, monoglycerol ethers of saturated and/or unsaturated, branched and/or straight-chain alcohols having a chain length of 8 to 24, in particular 12 to 18 C atoms, diglycerol ethers of saturated and/or unsaturated, branched and/or straight-chain alcohols having a chain length of 8 to 24, in particular 12 to 18 C atoms, propylene glycol esters of saturated and/or unsaturated, branched and/or straight-chain alkanecarboxylic acids having a chain length of 8 to 24, in particular 12 to 18 C atoms and sorbitan esters of saturated and/or unsaturated, branched and/or straight-chain alkanecarboxylic acids having a chain length of 8 to 24, in particular 12 to 18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol(2) stearyl ether (Steareth-2), glyceryl monolaurate, glyceryl monocaprinate, glyceryl monocaprylate.

Preferred embodiments and further aspects of the present invention can be seen from the appended patent claims and the following examples.

EXAMPLES

Example 1

Experiments to Determine the Tyrosinase-Inhibiting Action of Styrylresorcinol (4)

The finding that diphenylmethane derivatives of the Formula 1 (where R1-5 can each have the meanings indicated above) are outstanding for use as agents for skin lightening and for combating age spots results from the following experiments, which were carried out on 3T3 fibrosarcoma cells or B16V mouse melanoma cells.

A. (Cytotoxicity Determination)

3T3 fibrosarcoma cells or B16V mouse melanoma cells are distributed in a 96-well microtitre plate in a concentration of $1\times10^4$ cells/well (3T3) or $2\times10^4$ cells/well (B16V). After culturing for 24 h at 37° C. and 5% $CO_2$ in DMEM medium (3T3 cells) or RPMI medium (B16V cells), enriched with 10% foetal calf serum, the medium is removed by suction. Various concentrations of the test substances, dissolved in fresh medium enriched with 5% foetal calf serum, are added and the plates are incubated for a further 48 h. A parallel incubation is carried out using SDS as standard in concentrations of 0.01 mM, 0.1 mM, 1 mM and 10 mM. After the incubation, the medium is removed by suction and the cells are incubated for with (sic) 2 h with MTT (3-[4,5-dimethylthiazol-2-yl]2,5-diphenyl tetrazolium bromide). After extraction of the dye with SDS acidified with acetic acid in DMSO (10 min), the absorption (A) at 570 nm is measured.

Average value and standard deviation of the controls, the blanks and the samples are calculated. The average value of the blanks is substracted from the average values of the controls and samples. The viability of the cells is indicated as a percentage with respect to the controls (100%):

Viability (%)=$(A_{test\ compound}/A_{control})\times100]$

TABLE 1

Cytotoxicity (MTT/LDH assay, 3T3 fibroblasts and B16V mouse melanoma cells) - $IC_{50}$ and $IC_{20}$ values for styrylresorcinol, 4-hexylresorcinol and kojic acid.

| Test | 3T3 cells | | B16V cells | |
|---|---|---|---|---|
| substance | $IC_{20}$ | $IC_{50}$ | $IC_{20}$ | $IC_{50}$ |
| Kojic acid | >100 mM | >100 mM | >100 mM | >100 mM |
| 4-hexylresorcinol | 0.07 mM | 0.14 mM | n.d. | n.d. |
| Styrylresorcinol (4) | 0.07 mM | 0.15 mM | 0.02 mM | 0.14 mM | n.d.: not determined

The cytotoxicological experiments show that styrylresorcinol has a relatively low cytotoxicity, which is approximately comparable to the cytotoxicity of 4-hexylresorcinol, which, inter alia, is also used in food chemistry.

B: $IC_{50}$ Values for Styrylresorcinol (4) Compared with Kojic Acid and 4-Hexylresorcinol The $IC_{50}$ values of styrylresorcinol (4), kojic acid and 4-hexylresorcinol were determined in accordance with the general test conditions described below and summarised in Table 2.

Test method: B16V mouse melanoma cells are distributed in a 96-well micro titre plate in a concentration of $5\times10^3$ cells/well. After culturing for 24 h at 37° C. and 5% $CO_2$ in RPMI medium, enriched with 10% foetal calf serum, various concentrations of the test substances and 10 nM α-MSH (α-melanocyte stimulating hormone) are added and the plates are incubated for a further 96 h. The maximum concentration of the test substances used corresponds to 0.1 times the value of the particular $IC_{20}$ value from the cytotoxicity assay. A parallel incubation was carried out with kojic acid as standard in concentrations of 0.01 mM, 0.1 mM and 1 mM. After the incubation, SDS and NaOH (final concentrations: 1 mM and 1M, respectively) are added to the culture medium and the adsorption (A) is measured at 400 nm after 3 h.

The inhibition of the pigmentation in the presence of the test compounds or kojic acid was calculated in accordance with the following equation:

Inhibition of pigmentation (%)=$100-[(A_{test\ compound}/A_{control})\times100]$ The $IC_{50}$ is calculated for each test compound from the inhibition of the pigmentation (%) in a series of dilutions of test compounds. The $IC_{50}$ is the concentration of a test compound at which the pigmentation is 50% inhibited.

TABLE 2

Lightening effect (B16V mouse melanoma cells) - $IC_{50}$ values for styrylresorcinol, 4-hexylresorcinol and kojic acid

| Test substance | $IC_{50}$ (μM) |
|---|---|
| Kojic acid | 452.3 |
| Styrylresorcinol (4) | 2.1 |
| 4-hexylresorcinol | 5.2 |

As Table 2 shows, styrylresorcinol significantly inhibits the tyrosinase activity in very low concentrations and is thus outstandingly suitable for use as an agent for skin and hair lightening and for combating age spots. Compared with kojic acid, an active compound that is already frequently used in cosmetic products for skin and hair lightening and for controlling age spots, which, however, is not entirely toxicologically acceptable, styrylresorcinol (Formula 4) according to the invention has an activity that is greater by a factor of approximately 215. Compared with 4-hexylresorcinol, styrylresorcinol (Formula 4) still proves to be more than twice as effective. Accordingly, the effect of 4-hexylresorcinol compared with kojic acid is also only approximately 87 times as great.

The experiments discussed above clearly show that diphenylmethane derivatives of the Formula 1 (where R1 to R5 have the meanings indicated above and what has been stated above also applies in respect of the preferred meanings of R1 to R5) severely inhibit tyrosinase and thus are outstandingly suitable for use as skin and hair lightening agents, for combating age spots and/or as browning inhibitors in food chemistry.

The invention claimed is:

1. A topical tyrosinase inhibitor composition comprising a compound of the Formula 1 in an amount effective for skin lightening in humans, hair lightning in humans, combating age spots in human skin, or inhibiting browning in foods:

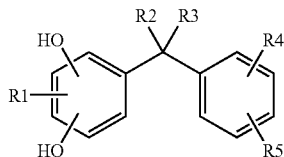

where:
R1 is hydrogen, methyl, straight-chain or branched, saturated or unsaturated alkyl having 2-4 C atoms, OH or halogen,
R2 is a straight-chain or branched, saturated or unsaturated alkyl having 2-5 C atoms,
R3 is methyl, and
R4 and R5 independently of one another are hydrogen, methyl, straight-chain or branched, saturated or unsaturated alkyl having 2-5 C atoms, OH or halogen, and
at least one member selected from the group consisting of a fragrance, a compound for care and/or cleansing of skin and/or hair, and a UV absorbing agent.

2. A process for skin lightening in humans and combating age spots in human skin comprising administering to a person in need thereof an effective amount of the tyrosinase inhibitor composition of claim 1.

3. A process for inhibiting browning of foods comprising applying to the food an effective amount of the tyrosinase inhibitor composition of claim 1.

4. The topical tyrosinase inhibitor composition of claim 1, wherein said fragrance is included in an amount effective to provide a sensory effect and said compound of Formula 1 is present in an amount of about 5 to 50% by mass.

5. The topical tyrosinase inhibitor composition of claim 1, wherein said UV absorbing filter is included in an amount effective to provide UV protection of at least greater than 2.

6. Fragrance composition, comprising
a) a fragrance in an amount that has a sensory effect,
b) one or more compounds of the Formula 1 in an amount that has an effect of inhibiting tyrosinase

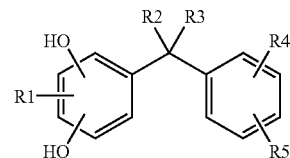

where:
R1 is hydrogen, methyl, straight-chain or branched, saturated or unsaturated alkyl having 2-4 C atoms, OH or halogen,
R2 is a straight-chain or branched, saturated or unsaturated alkyl having 2-5 C atoms,
R3 is methyl, and
R4 and R5 independently of one another are hydrogen, methyl, straight-chain or branched, saturated or unsaturated alkyl having 2-5 C atoms, OH or halogen.

7. Cosmetic formulation, comprising
one or more compounds for care and/or cleansing of (a) skin and/or (b) hair and
one or more compounds of the Formula 1 in an amount that has the effect of inhibiting tyrosinase

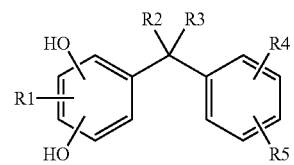

where:
R1 is hydrogen, methyl, straight-chain or branched, saturated or unsaturated alkyl having 2-4 C atoms, OH or halogen,
R2 is a straight-chain or branched, saturated or unsaturated alkyl having 2-5 C atoms,
R3 is methyl, and
R4 and R5 independently of one another are hydrogen, methyl, straight-chain or branched, saturated or unsaturated alkyl having 2-5 C atoms, OH or halogen.

8. Sunscreen formulation, comprising
an effective amount of a UV filter, so that the protection factor of the sunscreen formulation is greater than 2, and
one or more compounds of the Formula 1 in an amount that has the effect of inhibiting tyrosinase

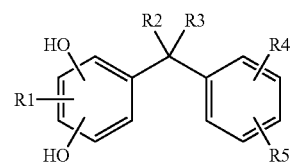

where:
R1 is hydrogen, methyl, straight-chain or branched, saturated or unsaturated alkyl having 2-4 C atoms, OH or halogen, R2 is a straight-chain or branched, saturated or unsaturated alkyl having 2-5 C atoms, R3 is methyl, and R4 and R5 independently of one another are hydrogen, methyl, straight-chain or branched, saturated or unsaturated alkyl having 2-5 C atoms, OH or halogen.

9. A process for preparing an agent for treatment (a) against skin and hair browning, (b) for combating age spots and/or (c) for the inhibition of the undesired browning of foods by adding to said agent a compound of the Formula 1

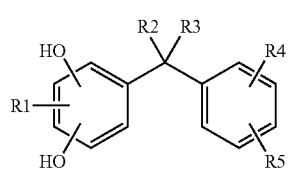

where:

R1 is hydrogen, methyl, straight-chain or branched, saturated or unsaturated alkyl having 2-4 C atoms, OH or halogen, R2 is a straight-chain or branched, saturated or unsaturated alkyl having 2-5 C atoms, R3 methyl, and R4 and R5 independently of one another are hydrogen, methyl, straight-chain or branched, saturated or unsaturated alkyl having 2-5 C atoms, OH or halogen.

* * * * *